US009833480B2

(12) United States Patent
Junghans et al.

(10) Patent No.: US 9,833,480 B2
(45) Date of Patent: Dec. 5, 2017

(54) METHODS AND COMPOSITIONS FOR TREATING HIV

(75) Inventors: Richard P. Junghans, Boston, MA (US); Nithianandan Selliah, Providence, RI (US)

(73) Assignee: Prospect Chartercare, LLC, Providence, RI (US)

( * ) Notice: Subject to any disclaimer, the term of this patent is extended or adjusted under 35 U.S.C. 154(b) by 1168 days.

(21) Appl. No.: 13/641,245

(22) PCT Filed: Apr. 14, 2011

(86) PCT No.: PCT/US2011/032455
§ 371 (c)(1),
(2), (4) Date: Apr. 5, 2013

(87) PCT Pub. No.: WO2011/130491
PCT Pub. Date: Oct. 20, 2011

(65) Prior Publication Data
US 2013/0183276 A1     Jul. 18, 2013

Related U.S. Application Data

(60) Provisional application No. 61/324,050, filed on Apr. 14, 2010.

(51) Int. Cl.
C07K 14/705 (2006.01)
A61K 35/30 (2015.01)
C07K 14/73 (2006.01)
A61K 48/00 (2006.01)
A61K 38/17 (2006.01)

(52) U.S. Cl.
CPC ........ *A61K 35/30* (2013.01); *C07K 14/70514* (2013.01); *A61K 38/1774* (2013.01); *A61K 48/00* (2013.01); *C07K 2319/03* (2013.01); *C07K 2319/33* (2013.01); *C07K 2319/735* (2013.01); *C07K 2319/74* (2013.01); *C07K 2319/90* (2013.01); *C12N 2799/027* (2013.01)

(58) Field of Classification Search
None
See application file for complete search history.

(56) References Cited

U.S. PATENT DOCUMENTS

| 5,686,281 | A | 11/1997 | Roberts |
| 9,206,440 | B2* | 12/2015 | Yang ............... C12N 15/86 |
| 2002/0165360 | A1 | 11/2002 | Junghans |
| 2003/0059944 | A1* | 3/2003 | Lois-Caballe ..... C12N 15/1132 |
| | | | 435/456 |
| 2003/0138410 | A1 | 7/2003 | Seed et al. |
| 2003/0152559 | A1 | 8/2003 | Yang et al. |
| 2003/0199093 | A1* | 10/2003 | Finer .................. C07K 14/005 |
| | | | 435/456 |
| 2006/0293262 | A1 | 12/2006 | Lieberman et al. |
| 2008/0096187 | A1 | 4/2008 | Shaw et al. |
| 2012/0134970 | A1* | 5/2012 | Yang .................. C12N 15/86 |
| | | | 424/93.21 |
| 2012/0148552 | A1 | 6/2012 | Jensen |
| 2014/0050708 | A1 | 2/2014 | Powell et al. |
| 2016/0083462 | A1* | 3/2016 | Yang .................. C07K 16/18 |
| | | | 424/93.2 |

FOREIGN PATENT DOCUMENTS

| WO | WO 2008/045437 A2 | 4/2008 |
| WO | WO 2010/085660 A2 | 7/2010 |
| WO | WO 2011/130491 A3 | 10/2011 |
| WO | WO2012099973 A2 | 7/2012 |

OTHER PUBLICATIONS

NCBI Accession No. NP_006130, 2015, 3 pages.*
Cullen, "Does RNA interference have a future as a treatment for H1V-1 induced disease?", Aids Rev., vol. 7, No. 1, pp. 22-25 (2005).
International Search Report from PCT Patent Application No. PCT/US2011/032455 mailed Sep. 8, 2011, application now published as International Publication No. WO2011/130491 on Oct. 20, 2011.
Jie et al., "The molecular cloning of porcine CD3 zeta", Uniprot Acc. No. Q9XSJ9, 1 page (1999).
Maher et al., "Human T-lymphocyte cytotoxicity and proliferation directed by a single chimeric TCRzeta/CD28 receptor", Nature Biotechnology, Nature Publishing Group, vol. 20, No. 1, pp. 70-75 (2002).
Marathe et al., "Is gene therapy a good therapeutic approach for HIV-positive patients?", Genetic Vaccines and Therapy, Biomed Central, vol. 5, No. 1, pp. 1-9 (2007).
Morris and Rossi, "Lentiviral-mediated delivery of siRNAs for antiviral therapy", Gene Ther., vol. 13, No. 6, pp. 553-558 (2006).
Roberts et al., "Targeting of human immunodeficiency virus-infected cells by CD8+T lymphocytes armed with universal t-cell receptors", Blood, American Society of Hematology, vol. 84, No. 9, pp. 2878-2889 (1994).
Rossi, "RNAi as a treatment for HIV-1 infection", BioTechniques, vol. 40, pp. s25-s29 (2006).
Yang et al., "Lysis of HIV-1-infected cells and inhibition of viral replication by universal receptor T cells", Proceedings of the National Academy of Sciences, vol. 94, No. 21, pp. 11478-11483 (1997).
Emtage et al., "2nd Generation anti-CEA designer t cells resist activation-induced cell death, proliferate on tumor contact, secrete cytokines and exhibit superior anti-tumor activity in vivo: a preclinical evaluation", Clin. Cancer Res., Dec. 15, 2008, vol. 14, No. 24, pp. 8112-8122.

(Continued)

*Primary Examiner* — Ilia Ouspenski

(74) *Attorney, Agent, or Firm* — McDermott Will & Emery LLP

(57) ABSTRACT

The invention features nucleic acid constructs encoding chimeric immune T-cell receptors (CIRs) that are useful for treating HIV in patients. In general, the CIRs contain an extracellular domain which targets HIV or HIV infected cells (e.g., the extracellular domain of CD4), a transmembrane domain, and a cytoplasmic domain for mediating T-cell activation (e.g., CD3 zeta and/or the partial extracellular domain of CD28). The invention also features the use of host cells expressing CIRs in the treatment of HIV.

20 Claims, 9 Drawing Sheets

(56) References Cited

OTHER PUBLICATIONS

Kohn et al., "CARs on Track in the Clinic," Mol. Ther., Mar. 2011, vol. 19, No. 3, pp. 432-438.
Maniappan et al., "Ligand-mediated cytolysis of tumor cells: use of heregulin-zeta chimeras to redirect cytotoxic T lymphocytes," Cancer Gene Therapy, 2000, vol. 7, No. 1, pp. 128-134.
Nekhai et al., "Therapies for HIV with RNAi," Curr Opin Mol Ter. Feb. 2006, vol. 8, No. 1, pp. 52-61.
Nolan et al., "Bypassing immunization: Optimized design of "Designer T Cells" against carcinoembryonic antigen (CEA)-expressing tumors, and lack of suppression by soluble CEA", Clinical Cancer Res., Dec. 1999, vol. 5, pp. 3928-3941.
Sadelain et al., "The promise and potential pitfalls of chimeric antigen receptors", Curr. Opin. Immunol., 2009, vol. 21, No. 2, pp. 215-223.
International Preliminary Report on Patentability from PCT Patent Application No. PCT/US2011/032455 dated Oct. 16, 2012, application now published as International Publication No. WO2011130491 dated Oct. 20, 2011.

* cited by examiner

A.

B.

SEQUENCE LISTING

```
<160> NUMBER OF SEQ ID NOS: 12

<210> SEQ ID NO 1
<211> LENGTH: 458
<212> TYPE: PRT
<213> ORGANISM: Homo sapiens

<400> SEQUENCE: 1

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
```

```
                35                  40                  45
Ile Gln Phe His Trp Lys Asn Ser Asn Gln Ile Lys Ile Leu Gly Asn
            50                  55                  60
Gln Gly Ser Phe Leu Thr Lys Gly Pro Ser Lys Leu Asn Asp Arg Ala
 65                  70                  75                  80
Asp Ser Arg Arg Ser Leu Trp Asp Gln Gly Asn Phe Pro Leu Ile Ile
                85                  90                  95
Lys Asn Leu Lys Ile Glu Asp Ser Asp Thr Tyr Ile Cys Glu Val Glu
            100                 105                 110
Asp Gln Lys Glu Glu Val Gln Leu Leu Val Phe Gly Leu Thr Ala Asn
        115                 120                 125
Ser Asp Thr His Leu Leu Gln Gly Gln Ser Leu Thr Leu Thr Leu Glu
    130                 135                 140
Ser Pro Pro Gly Ser Ser Pro Ser Val Gln Cys Arg Ser Pro Arg Gly
145                 150                 155                 160
Lys Asn Ile Gln Gly Gly Lys Thr Leu Ser Val Ser Gln Leu Glu Leu
                165                 170                 175
Gln Asp Ser Gly Thr Trp Thr Cys Thr Val Leu Gln Asn Gln Lys Lys
            180                 185                 190
Val Glu Phe Lys Ile Asp Ile Val Val Leu Ala Phe Gln Lys Ala Ser
        195                 200                 205
Ser Ile Val Tyr Lys Lys Glu Gly Glu Gln Val Glu Phe Ser Phe Pro
    210                 215                 220
Leu Ala Phe Thr Val Glu Lys Leu Thr Gly Ser Gly Glu Leu Trp Trp
225                 230                 235                 240
Gln Ala Glu Arg Ala Ser Ser Ser Lys Ser Trp Ile Thr Phe Asp Leu
                245                 250                 255
Lys Asn Lys Glu Val Ser Val Lys Arg Val Thr Gln Asp Pro Lys Leu
            260                 265                 270
Gln Met Gly Lys Lys Leu Pro Leu His Leu Thr Leu Pro Gln Ala Leu
        275                 280                 285
Pro Gln Tyr Ala Gly Ser Gly Asn Leu Thr Leu Ala Leu Glu Ala Lys
    290                 295                 300
Thr Gly Lys Leu His Gln Glu Val Asn Leu Val Val Met Arg Ala Thr
305                 310                 315                 320
Gln Leu Gln Lys Asn Leu Thr Cys Glu Val Trp Gly Pro Thr Ser Pro
                325                 330                 335
Lys Leu Met Leu Ser Leu Lys Leu Glu Asn Lys Glu Ala Lys Val Ser
            340                 345                 350
Lys Arg Glu Lys Ala Val Trp Val Leu Asn Pro Glu Ala Gly Met Trp
        355                 360                 365
Gln Cys Leu Leu Ser Asp Ser Gly Gln Val Leu Leu Glu Ser Asn Ile
    370                 375                 380
Lys Val Leu Pro Thr Trp Ser Thr Pro Val Gln Pro Met Ala Leu Ile
385                 390                 395                 400
Val Leu Gly Gly Val Ala Gly Leu Leu Leu Phe Ile Gly Leu Gly Ile
                405                 410                 415
Phe Phe Cys Val Arg Cys Arg His Arg Arg Arg Gln Ala Glu Arg Met
            420                 425                 430
Ser Gln Ile Lys Arg Leu Leu Ser Glu Lys Lys Thr Cys Gln Cys Pro
        435                 440                 445
His Arg Phe Gln Lys Thr Cys Ser Pro Ile
    450                 455
```

<210> SEQ ID NO 2
<211> LENGTH: 220
<212> TYPE: PRT
<213> ORGANISM: Homo sapiens

<400> SEQUENCE: 2

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
            115                 120                 125

Asn Gly Thr Ile Ile His Val Lys Gly Lys His Leu Cys Pro Ser Pro
        130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
        210                 215                 220

<210> SEQ ID NO 3
<211> LENGTH: 163
<212> TYPE: PRT
<213> ORGANISM: Homo sapiens

<400> SEQUENCE: 3

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
        50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140

Ser Thr Ala Thr Lys Asp Thr Tyr Asp Ala Leu His Met Gln Ala Leu
145                 150                 155                 160

Pro Pro Arg

<210> SEQ ID NO 4
<211> LENGTH: 10
<212> TYPE: PRT
<213> ORGANISM: Homo sapiens

<400> SEQUENCE: 4

Glu Gln Lys Leu Ile Ser Glu Glu Asp Leu
1               5                   10

<210> SEQ ID NO 5
<211> LENGTH: 21
<212> TYPE: RNA
<213> ORGANISM: Human immunodeficiency virus

<400> SEQUENCE: 5
gcggagacag cgacgaagag c                                           21

<210> SEQ ID NO 6
<211> LENGTH: 19
<212> TYPE: RNA
<213> ORGANISM: Homo sapiens

<400> SEQUENCE: 6
gccugggaga gcuggggaa                                              19

<210> SEQ ID NO 7
<211> LENGTH: 277
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
tcaggtggtg gcggttcagg cggaggtggc tctggcggtg gcggatcggc ccggatagct     60
cagtcggtag agcacagact ttaatctgag ggtccaggt caagtccctg ttcgggcgcc    120
agcctgggag agctggggaa tttgtacgta gttccccagc tctcccaggc ggtggcagtg    180
gctccggagg ttcaggaagc ggcggtagtg ggagcgcgga gacagcgacg aagagccttc    240
ctgtcagagc ggagacagcg acgaagagct ttttgaa                            277

<210> SEQ ID NO 8
<211> LENGTH: 1602
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgaaccggg gagtcccttt taggcacttg cttctggtgc tgcaactggc gctcctccca     60
gcagccactc agggagagca gaagctgatc tccgaggagg acctgaagaa agtggtgctg    120

```
ggcaaaaaag gggatacagt ggaactgacc tgtacagctt cccagaagaa gagcatacaa      180
ttccactgga aaactccaa ccagataaag attctgggaa atcagggctc cttcttaact       240
aaaggtccat ccaagctgaa tgatcgcgct gactcaagaa gaagcctttg ggaccaagga      300
aactttcccc tgatcatcaa gaatcttaag atagaagact cagatactta catctgtgaa      360
gtggaggacc agaaggagga ggtgcaattg ctagtgttcg gattgactgc caactctgac      420
acccacctgc ttcaggggca gagcctgacc ctgaccttgg agacccccc tggtagtagc       480 ccctcagtgc aatgtaggag tccaagggg aaaaacatac aggggggaa gaccctctcc       540 gtgtctcagc tggagctcca ggatagtggc acctggacat gcactgtctt gcagaaccag      600
aagaaggtgg agttcaaaat agacatcgtg gtgctagctt tccagaaggc ctccagcata      660
gtctataaga agagggga acaggtggag ttctccttcc cactcgcctt tacagttgaa        720
aagctgacgg gcagtggcga gctgtggtgg caggcggaga gggcttcctc ctccaagtct      780
tggatcacct ttgacctgaa gaacaaggaa gtgtctgtaa acgggttac ccaggaccct       840 aagctccaga tgggcaagaa gctcccgctc cacctcaccc tgccccaggc cttgcctcag      900
tatgctggct ctggaaacct cacccctggcc cttgaagcga aaacaggaaa gttgcatcag    960
gaagtgaacc tggtggtgat gagagccact cagctccaga aaatttgac ctgtgaggtg      1020 tggggacccca cctcccctaa gctgatgctg agcttgaaac tggagaacaa ggaggcaaag    1080
gtctcgaagc gggagaaggc ggtgtgggtg ctgaaccctg aggcgggat gtggcagtgt      1140 ctgctgagtg actcgggaca ggtcctgctg gaatccaaca tcaaggttct gcccacatgg    1200 tccacccgg tgcctaggct ggatcccaaa ctctgctacc tgctggatgg aatcctcttc     1260
atctatggtg tcattctcac tgccttgttc ctgagagtga agttcagcag gagcgcagac     1320 gccccgcgt accagcaggg ccagaaccag ctctataacg agctcaatct aggacgaaga       1380
gaggagtacg atgttttgga caagagacgt ggccgggacc ctgagatggg gggaaagccg     1440
agaaggaaga accctcagga aggcctgtac aatgaactgc agaaagataa gatggcggag     1500
gcctacagtg agattgggat gaaaggcgag cgccggaggg gcaaggggca cgatggcctt     1560
taccagggtc tcagtacagc caccaaggac acctacgacg cc                      1602
```

<210> SEQ ID NO 9
<211> LENGTH: 1851
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
atgaaccggg gagtcccttt taggcacttg cttctggtgc tgcaactggc gctcctccca      60
gcagccactc agggagagca gaagctgatc tccgaggagg acctgaagaa agtggtgctg     120
ggcaaaaaag gggatacagt ggaactgacc tgtacagctt cccagaagaa gagcatacaa      180
ttccactgga aaactccaa ccagataaag attctgggaa atcagggctc cttcttaact       240
aaaggtccat ccaagctgaa tgatcgcgct gactcaagaa gaagcctttg ggaccaagga      300
aactttcccc tgatcatcaa gaatcttaag atagaagact cagatactta catctgtgaa      360
gtggaggacc agaaggagga ggtgcaattg ctagtgttcg gattgactgc caactctgac      420
acccacctgc ttcaggggca gagcctgacc ctgaccttgg agacccccc tggtagtagc       480 ccctcagtgc aatgtaggag tccaagggg aaaaacatac aggggggaa gaccctctcc       540
```

-continued

```
gtgtctcagc tggagctcca ggatagtggc acctggacat gcactgtctt gcagaaccag      600
aagaaggtgg agttcaaaat agacatcgtg gtgctagctt ccagaaggc ctccagcata       660 gtctataaga aagagggga acaggtggag ttctccttcc cactcgcctt tacagttgaa      720
aagctgacgg gcagtggcga gctgtggtgg caggcggaga gggcttcctc ctccaagtct      780
tggatcacct ttgacctgaa gaacaaggaa gtgtctgtaa acgggttac ccaggaccct      840 aagctccaga tgggcaagaa gctcccgctc cacctcaccc tgccccaggc cttgcctcag      900
tatgctggct ctggaaacct caccctggcc cttgaagcga aaacaggaaa gttgcatcag      960
gaagtgaacc tggtggtgat gagagccact cagctccaga aaatttgac ctgtgaggtg      1020 tggggaccca cctcccctaa gctgatgctg agcttgaaac tggagaacaa ggaggcaaag      1080
gtctcgaagc gggagaaggc ggtgtgggtg ctgaaccctg aggcggggat gtggcagtgt     1140
ctgctgagtg actcgggaca ggtcctgctg gaatccaaca tcaaggttct gcccacatgg     1200
tccacccggg tgcctaggaa aattgaagtt atgtatcctc ctccttacct agacaatgag     1260
aagagcaatg gaaccattat ccatgtgaaa gggaaacacc tttgtccaag tcccctattt     1320
cccggacctt ctaagccctt ttgggtgctg gtggtggttg gtggagtcct ggcttgctat     1380
agcttgctag taacagtggc cttattatt ttctgggtga ggagtaagag gagcaggctc      1440
ctgcacagtg actacatgaa catgactccc cgccgccccg ggcccacccg caagcattac     1500
cagccctatg ccccaccacg cgacttcgca gcctatcgct ccagagtgaa gttcagcagg    1560
agcgcagacg cccccgcgta ccagcagggc cagaaccagc tctataacga gctcaatcta    1620
ggacgaagag aggagtacga tgttttggac aagagacgtg gccgggaccc tgagatgggg    1680
ggaaagccga aaggaagaa ccctcaggaa ggcctgtaca atgaactgca gaaagataag     1740
atggcggagg cctacagtga gattgggatg aaaggcgagc gccggagggg caaggggcac    1800
gatggccttt accagggtct cagtacagcc accaaggaca cctacgacgc c             1851
```

<210> SEQ ID NO 10
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Lys Ile Glu Val Met Tyr Pro Pro Tyr Leu Asp Asn Glu Lys Ser
1               5                   10                  15

Asn Gly Thr Ile Ile His Val Lys Gly Lys His Leu Cys Pro Ser Pro
            20                  25                  30

Leu Phe Pro Gly Pro Ser Lys Pro Phe Trp Val Leu Val Val Val Gly
        35                  40                  45

Gly Val Leu Ala Cys Tyr Ser Leu Leu Val Thr Val Ala Phe Ile Ile
    50                  55                  60

Phe Trp Val Arg Ser Lys Arg Ser Arg Leu Leu His Ser Asp Tyr Met
65                  70                  75                  80

Asn Met Thr Pro Arg Arg Pro Gly Pro Thr Arg Lys His Tyr Gln Pro
                85                  90                  95

Tyr Ala Pro Pro Arg Asp Phe Ala Ala Tyr Arg Ser Arg Val Lys Phe
            100                 105                 110

Ser Arg Ser Ala Asp Ala Pro Ala Tyr Gln Gln Gly Gln Asn Gln Leu
        115                 120                 125
```

```
Tyr Asn Glu Leu Asn Leu Gly Arg Arg Glu Glu Tyr Asp Val Leu Asp
    130                 135                 140
Lys Arg Arg Gly Arg Asp Pro Glu Met Gly Gly Lys Pro Arg Arg Lys
145                 150                 155                 160
Asn Pro Gln Glu Gly Leu Tyr Asn Glu Leu Gln Lys Asp Lys Met Ala
                165                 170                 175
Glu Ala Tyr Ser Glu Ile Gly Met Lys Gly Glu Arg Arg Arg Gly Lys
                180                 185                 190
Gly His Asp Gly Leu Tyr Gln Gly Leu Ser Thr Ala Thr Lys Asp Thr
            195                 200                 205
Tyr Asp Ala
    210

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser Gly Gly Gly Gly Ser Gly Gly Gly Gly Ser
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Ser Gly Ser Gly Gly Ser Gly Ser Gly Gly Ser Gly Ser
1               5                   10                  15
```

METHODS AND COMPOSITIONS FOR TREATING HIV

CROSS-REFERENCE TO RELATED APPLICATIONS

This application is the U.S. National Stage of PCT/US2011/032455, filed Apr. 14, 2011, which, in turn, claims benefit of U.S. Provisional Application No. 61/324,050, filed Apr. 14, 2010, which is hereby incorporated by reference.

STATEMENT REGARDING FEDERALLY SPONSORED RESEARCH

This invention was made with Government support under contract R21 AI076145 awarded by the National Institutes of Health. The government has certain rights in this invention.

BACKGROUND OF THE INVENTION

The invention relates to the field of treating HIV with modified T-cells.

In 1984, HIV was shown to be the etiologic agent of AIDS. Since that time, the definition of AIDS has been revised a number of times with regard to what criteria should be included in the diagnosis. However, despite the fluctuation in diagnostic parameters, the simple common denominator of AIDS is the infection with HIV and subsequent development of persistent constitutional symptoms and AIDS-defining diseases such as a secondary infections, neoplasms, and neurologic disease.

HIV is a human retrovirus of the lentivirus group. The four recognized human retroviruses belong to two distinct groups: the human T lymphotropic (or leukemia) retroviruses, HTLV-1 and HTLV-2, and the human immunodeficiency viruses, HIV-1 and HIV-2. The former are transforming viruses whereas the latter are cytopathic viruses.

HIV-1 has been identified as the most common cause of AIDS throughout the world. Sequence identity between HIV-2 and HIV-1 is about 40%, with HIV-2 being more closely related to some members of a group of simian immunodeficiency viruses (SIV).

The main cause of the immune defect in AIDS has been identified as a quantitative and qualitative deficiency in the subset of thymus-derived (T) lymphocytes, the T4 population. This subset of cells is defined phenotypically by the presence of the CD4 surface molecule, which has been demonstrated to be the cellular receptor for HIV. Although the T4 cell is the major cell type infected with HIV, essentially any human cell that expresses the CD4 molecule on its surface is capable of binding to and being infected with HIV.

Previous attempts to treat patients with "designer" T-cells expressing chimeric immune receptors (CIRs) proved unsuccessful. There exists a need in the art for new therapies for HIV. The present invention addresses this issue and offers advantages over previous attempted therapies.

SUMMARY OF THE INVENTION

In one aspect, the invention features a nucleic acid construct encoding a chimeric protein that includes (i) an extracellular domain of CD4 (e.g., amino acids 1-372 of SEQ ID NO:1) or a fragment thereof, (ii) a transmembrane domain, and (iii) a cytoplasmic domain that includes the cytoplasmic domain of the CD3 zeta chain (e.g., a polypeptide having the amino acids 31-142 of SEQ ID NO:3), or a fragment thereof, and the cytoplasmic domain of CD28 (e.g., a polypeptide having amino acids 127-234 of SEQ ID NO:2), or a fragment thereof. In one embodiment, the cytoplasmic domain has the amino acid sequence of SEQ ID NO:10.

In another aspect, the invention features a nucleic acid construct encoding a chimeric protein that includes (i) an extracellular domain of CD4 (e.g., a polypeptide having amino acids 1-372 of SEQ ID NO:1) or a fragment thereof, (ii) a transmembrane domain, and (iii) a cytoplasmic domain of the CD3 zeta chain (e.g., a polypeptide having the amino acids 31-142 of SEQ ID NO:3), or a fragment thereof.

In either of the foregoing aspects, the chimeric protein can be capable of forming a homodimer when expressed in a T-cell, e.g., through the formation of a disulfide bond.

Also in either of the foregoing aspects, the transmembrane domain can be the transmembrane domain of the CD3 zeta chain (e.g., a polypeptide having amino acids 7-30 of SEQ ID NO:3) or the transmembrane/partial extracellular domain of CD28.

Also in either of the foregoing aspects, the chimeric protein can include a c-myc tag (e.g., at the N-terminus).

In another aspect, the invention features a vector including any of the nucleic acid constructs described above. This vector can also include a nucleic acid construct encoding an siRNA (e.g., against CCR5 or against Tat/Rev).

In yet another aspect, the invention features a host cell (e.g., a T-cell derived from an uninfected patient or T-cell derived from a patient infected with HIV) containing any of the above nucleic acid constructs or vectors. This host cell can also include a nucleic acid construct encoding an siRNA (e.g., against CCR5 or against Tat/Rev).

In another aspect, the invention features a method of treating a patient infected with HIV (e.g., HIV-1 or HIV-2) by administering a composition including any of the foregoing host cells. In this aspect, the host cell can be isolated from the patient being treated or from another patient.

By "specifically binds" is meant an extracellular domain which recognizes and binds an HIV protein, but that does not substantially recognize and bind other molecules in a sample, e.g., a human blood sample.

By "treating" is meant ameliorating a condition or symptom(s) of the condition (e.g., the symptoms of HIV infection). To "treat HIV" or refers to administering a treatment to a subject infected with HIV to improve the subject's condition. As compared with an equivalent untreated control, such amelioration or degree of treatment is at least 5%, 10%, 20%, 30%, 40%, 50%, 60%, 70%, 80%, 90%, 95%, 99%, or 100%, as measured by the subject's HIV viral load.

By "vector" is meant a DNA molecule, usually derived from a plasmid or bacteriophage, into which fragments of DNA may be inserted or cloned. A recombinant vector will contain one or more unique restriction sites, and may be capable of autonomous replication in a defined host or vehicle organism such that the cloned sequence is reproducible. A vector contains a promoter operably-linked to a gene or coding region such that, upon transfection into a recipient cell, an RNA or an encoded protein or is expressed.

By "host T-cell" is meant a cell (e.g., a human T-cell isolated from a subject) into which one or more nucleic acid constructs is introduced.

By "chimeric immune T-cell receptor" or "CIR" is meant a fusion protein which, when expressed in a host T cell, contains an extracellular domain that specifically binds to a target protein and a cytoplasmic domain that modulates activation of the host T-cell.

By "CD4 extracellular domain" is meant a polypeptide having the N-terminal region of CD4 that is located outside the cell membrane when expressed in a T-cell, e.g., a polypeptide having the amino acid sequence of amino acids 1-372 of SEQ ID NO:1. The term "CD4 extracellular domain" is also meant to include any polypeptide fragment that binds specifically to gp120 and is substantially identical to amino acids 1-372 of SEQ ID NO:1 over the length of the polypeptide fragment.

| SEQ ID NO: 1 Human CD4 Amino Acid sequence |
|---|

```
LOCUS       NP_000607                458 aa            linear   PRI
18 Mar. 2010
DEFINITION  T-cell surface glycoprotein CD4 precursor [Homo sapiens].
ACCESSION   NP_000607
VERSION     NP_000607.1  GI: 10835167
DBSOURCE    REFSEQ: accession NM_000616.3

1 MNRGVPFRHL LLVLQLALLP AATQGKKVVL GKKGDTVELT CTASQKKSIQ FHWKNSNQIK
   61 ILGNQGSFLT KGPSKLNDRA DSRRSLWDQG NFPLIIKNLK IEDSDTYICE VEDQKEEVQL
  121 LVFGLTANSD THLLQGQSLT LTLESPPGSS PSVQCRSPRG KNIQGGKTLS VSQLELQDSG
  181 TWTCTVLQNQ KKVEFKIDIV VLAFQKASSI VYKKEGEQVE FSFPLAFTVE KLTGSGELWW
  241 QAERASSSKS WITFDLKNKE VSVKRVTQDP KLQMGKKLPL HLTLPQALPQ YAGSGNLTLA
  301 LEAKTGKLHQ EVNLVVMRAT QLQKNLTCEV WGPTSPKLML SLKLENKEAK VSKREKAVWV
  361 LNPEAGMWQC LLSDSGQVLL ESNIKVLPTW STPVQPMALI VLGGVAGLLL FIGLGIFFCV
  421 RCRHRRRQAE RMSQIKRLLS EKKTCQCPHR FQKTCSPI
```

By "CD28 cytoplasmic domain" is meant a polypeptide having the C-terminal region of CD28 that is located in the cytoplasm when expressed in a T-cell, e.g., a polypeptide having the amino acid sequence of amino acids 180-220 of SEQ ID NO:2. The term "CD28 cytoplasmic domain" is also meant to include any polypeptide fragment that maintains the ability to modulate activation of T-cells (e.g., as determined using the method titled "killing of HIV infected cells by modified T-cells" below) and is substantially identical to amino acids 180-220 of SEQ ID NO:2 over the length of the polypeptide fragment.

stranded that is at least 15 nucleotides, preferably, 17, 18, 19, 20, 21, 22, 23, 24, 25, 26, 27, 28, 29, 30, 31, 32, 33, 34, or 35 nucleotides in length and even up to 50 or 100 nucleotides in length (inclusive of all integers in between). Preferably, the siRNA is capable of mediating RNAi. As used herein the phrase "mediates RNAi" refers to (indicates) the ability to distinguish which RNAs are to be degraded by the RNAi machinery or process. siRNAs are processed from long dsRNAs and are usually double-stranded (e.g., endogenous siRNAs). siRNAs can also include short hairpin RNAs in which both strands of an siRNA duplex are

| SEQ ID NO: 2 Human CD28 Amino Acid sequence: |
|---|

```
LOCUS       NP_006130                220 aa            linear   PRI
11 Apr. 2010
DEFINITION  T-cell-specific surface glycoprotein CD28 precursor
            [Homo sapiens].
ACCESSION   NP_006130
VERSION     NP_006130.1  GI: 5453611
DBSOURCE    REFSEQ: accession NM_006139.2

1 MLRLLLALNL FPSIQVTGNK ILVKQSPMLV AYDNAVNLSC KYSYNLFSRE FRASLHKGLD
   61 SAVEVCVVYG NYSQQLQVYS KTGFNCDGKL GNESVTFYLQ NLYVNQTDIY FCKIEVMYPP
   21 PYLDNEKSNG TIIHVKGKHL CPSPLFPGPS KPFWVLVVVG GVLACYSLLV TVAFIIFWVR
  181 SKRSRLLHSD YMNMTPRRPG PTRKHYQPYA PPRDFAAYRS
```

By "CD3 zeta" is meant a polypeptide having the amino acid sequence of SEQ ID NO:3. The term "CD3 zeta" is also meant to include any polypeptide fragment that maintains the ability to modulate activation of T-cells (e.g., as determined using the method titled "killing of HIV infected cells by modified T-cells" below) and is substantially identical to SEQ ID NO:3 over the length of the protein fragment.

included within a single RNA molecule. These terms include double-stranded RNA, single-stranded RNA, isolated RNA, as well as altered RNA that differs from naturally occurring RNA by the addition, deletion, substitution, and/or alteration of one or more nucleotides.

By "substantially identical" is meant a nucleic acid or amino acid sequence that, when optimally aligned, for

| SEQ ID NO: 3 Human CD3 zeta Amino Acid sequence |
|---|

```
LOCUS       NP_000725                163 aa            linear   PRI
11 Apr. 2010
DEFINITION  T-cell receptor zeta chain isoform 2 precursor [Homo
            sapiens].
ACCESSION   NP_000725
VERSION     NP_000725.1  GI: 4557431
DBSOURCE    REFSEQ: accession NM_000734.3

1 MKWKALFTAA ILQAQLPITE AQSFGLLDPK LCYLLDGILF IYGVILTALF LRVKFSRSAD
   61 APAYQQGQNQ LYNELNLGRR EEYDVLDKRR GRDPEMGGKP RRKNPQEGLY NELQKDKMAE
  121 AYSEIGMKGE RRRGKGHDGL YQGLSTATKD TYDALHMQAL PPR
```

By "small interfering RNA" or "siRNA" is meant an isolated RNA molecule, either single-stranded or double example using the methods described below, share at least 60%, 65%, 70%, 75%, 80%, 85%, 90%, 95%, 96%, 97%, 98%, 99%, or 100% sequence identity with a second nucleic acid or amino acid sequence. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith and Waterman (1981) J Mol Biol 147:195-7); "BestFit" (Smith and Waterman, Advances in Applied Mathematics, (1981) 482-489) as incorporated into GeneMatcher Plus™, Schwarz and Dayhof, Atlas of Protein Sequence and Structure, Dayhof, M. O., Ed (1979) 353-358; BLAST program (Basic Local Alignment Search Tool; (Altschul et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the full length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Other features and advantages of the invention will be apparent from the following Detailed Description, the drawings, and the claims.

DETAILED DESCRIPTION OF THE INVENTION

Figure 1:
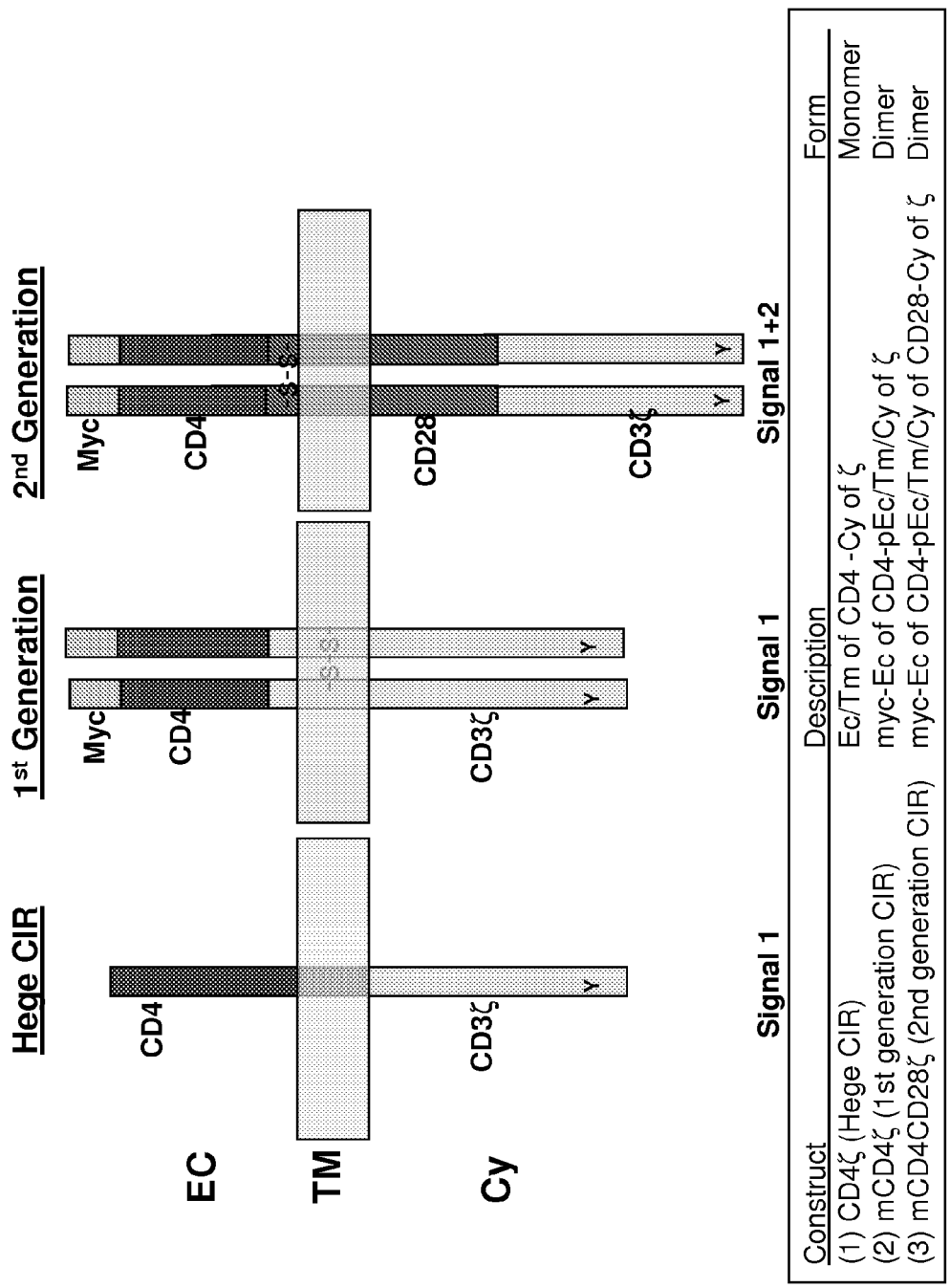
FIG. 1 is a diagram showing the structure of the indicated chimeric immune T-cell receptors (CIRs).

The invention features nucleic acid constructs encoding chimeric immune T-cell receptors (CIRs) that are useful for treating HIV in patients. In general, the CIRs contain an extracellular domain which targets HIV or HIV-infected cells (e.g., the extracellular domain of CD4), a transmembrane domain, and a cytoplasmic domain for mediating T-cell activation (e.g., CD3 zeta and/or the partial extracellular domain of CD28). The invention also features the use of host cells expressing CIRs in the treatment of HIV. When expressed in the host cells, the CIRs can be engineered to homodimerize, thereby increasing their potency. These host cells can also contain nucleic acid constructs encoding siRNA against HIV genes in order to, e.g., disrupt HIV infection of the host T-cells. The structure of a prior art CIR and the structures of CIRs containing the transmembrane domain of CD3 zeta and partially extracellular domain of CD28 are depicted in FIG. 1.

Extracellular Domains

The CIRs of the invention feature an extracellular domain able to specifically bind HIV and cells infected with HIV.

The HIV protein gp120 binds human CD4. Therefore, the extracellular domain of the CIRs of the invention can include the extracellular domain of CD4 (e.g., human CD4 or fragments thereof). Alternatively, the extracellular domain can include any binding moiety specific for HIV and cells infected with HIV, including, HIV specific antibodies (e.g., single-chain Fv antibody fragments that are specific to gp120 or gp41).

The extracellular domain can optionally include a further protein tag, e.g., a c-myc tag (EQKLISEEDL (SEQ ID NO:4) of human origin, at the N-terminus. The c-myc tag does not obstruct CD4 binding to gp120. Inclusion of c-myc in the sFv based-CIR design does not appear to affect CIR function, but can facilitate future study of the construct.

Cytoplasmic Domains

The CIRs of the invention also feature a cytoplasmic domain for signaling modulating activation of the host T-cells when bound to HIV or HIV-infected cells. Cytoplasmic domains useful for use in the CIRs of the invention include CD3 zeta, or fragments thereof, and for the cytoplasmic domain of CD28, or fragments thereof. The invention also features the fusion of polypeptides derived from multiple extracellular domains for potentiating activation of T-cells when bound to HIV or HIV-infected cells (e.g., a cytoplasmic domain that includes both active fragments of CD3 zeta and CD28).

Transmembrane Domains

The CIRs of the invention feature transmembrane domains derived from CD4, CD28, CD3 zeta, or another protein. Furthermore, the transmembrane domain (or the partial extracellular domains, "pEC") can be engineered to facilitate homodimerization of the CIRs when expressed in host T-cells. This can be accomplished, e.g., with the addition or substitution of cysteine residues capable of forming disulfide bonds with a paired molecule.

The inclusion of the transmembrane region of the zeta chain or the transmembrane and partial extracellular domain of CD28 provides the capability of intermolecular disulfide bonds. CIRs containing these transmembrane/partial extracellular domains are predicted to form disulfide-linked dimers through a cysteine residue located in the transmembrane of zeta or in the proximal cysteine residue located in the partial extracellular domain of CD28 (position 123 of CD28), mimicking the dimer configuration of native zeta and CD28.

siRNA Constructs

The DNA constructs and host cells of the invention also optionally feature components to suppress HIV infection of host T-cells. Such components include siRNA constructs for suppression of HIV replication. These siRNA constructs can be specific for various HIV targets (reviewed in Morris (2006) Gene Ther 13:553-558; Rossi (2006) Biotechniques Suppl:25-29; Nekhai (2006) Curr Opin Mol Ther 8:52-61; and Cullen (2005) AIDS Rev 7:22-25). One example is an siRNA targeting a highly conserved sequence in an exon common to both tat and rev, has been shown to be effective to prevent virus expression and replication (See, e.g., SEQ ID No. 1). In order to prevent HIV infection of host T-cells, the invention also features components to decrease expression of T cell coreceptors (e.g., CCR5 and CCR4). Such suppression would be expected to hinder infection of host T-cells as people with CCR5Δ32 mutation are resistant to HIV infection. The invention also features the inclusion of multiple siRNA constructs (e.g., constructs against HIV genes and T-cell receptors used for HIV infection). Here, one siRNA construct can block infection and while a second siRNA construct prevents progression of infection.

Figure 2:
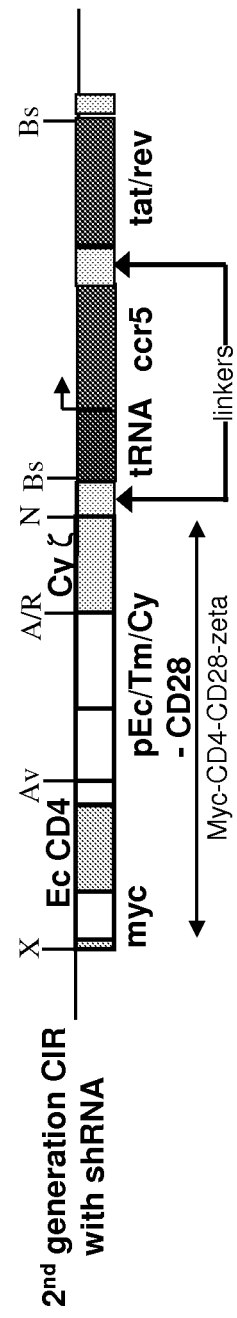
FIG. 2 is a diagram showing the organization of an exemplary nucleic acid construct encoding a $2^{nd}$ generation CIR and siRNA construct.

Methods of designing and expressing siRNA constructs are well known in the art. For example, the siRNA constructs of the invention can utilize long-hairpin RNA (lhRNA) to express both CCR5 and Tat/Rev siRNAs. Use of a lhRNA is a viable approach in controlling HIV-1 replication since a single long transcript can in theory be processed into multiple siRNAs. Multiple targeting can be achieved from a single long-hairpin precursor, suggesting that multiple siRNAs can be processed from the long hairpins in vivo. The siRNA constructs of the invention can also include a promoter directing expression in host T-cells. Examples of such promoters are U6 and tRNA promoters. Expressing shRNAs from tRNA promoters has several advantages, compared to the more commonly used U6 and H1 promoters: tRNA promoters are smaller, provide a variety of options, and are typically expressed at lower levels. Smaller promoters may be desirable in the nucleic acid constructs of the invention to facilitate inclusion in a vector including a CIR expression construct. An example of a nucleic acid construct containing a CIR and siRNA is set forth in FIG. 2.

```
shRNA sequences
tat/rev shRNA-sense strand
                                                            SEQ ID NO: 5
5'-GCGGAGACAGCGACGAAGAGC-3'
Ref: Scherer, L. J., R. Frank, and J. J. Rossi. 2007. Nucleic Acids
Res 35: 2620-2628.

ccr5 shRNA-sense strand
                                                            SEQ ID NO: 6
5' - GCCUGGGAGAGCUGGGGAA - 3'
Ref: Ehsani, Mol Ther Epub ahead of print.

shRNA within CIR
                                                           (SEQ ID NO: 7)
-Myc-CD4-CD28-zeta-tcaggtggtggcggttcaggcggaggtggctctggcggtggcggatcg
                                                      Generic linker (G4S)3

GCCCGGATAGCTCAGTcGGTAGAGCACAGACTTTAATCTGAGGGTCCAGGGTCAAGTCCCTGTTCGGGC
                                    tRNA promoter

GCCA

GCCTGGGAGAGCTGGGGAATTTGTACGTAGTTCCCCAGCTCTCCCAGGC
ccr5 shRNA sense     shRNA loop   ccr5 shRNA antisense
```

-continued

<u>ggtggcagtggctccggaggttcaggaagcggcggtagtgggagc</u>
          generic linker (GGSGS)3

GCGGAGACAGCGACGAAGAGC<u>CTTCCTGTCAGA</u>GCGGAGACAGCGACGAAGAGC<u>TTTTTGAA</u>
tat/rev shRNA sense    shRNA loop   tat/rev shRNA    terminator
                                      antisense      sequence

Nucleic Acid Constructs

The nucleic acid constructs of the invention are useful for expressing CIRs and siRNA constructs in host T-cells. CIRs and siRNA constructs can be included in a single nucleic acid construct or multiple nucleic acid constructs. In order to facilitate transfection of host cells, the nucleic acid construct can be included in a viral vector (e.g., a retroviral vector or adenoviral vector) or be designed to be transfected into a host cell via electroporation or chemical means (e.g., using a lipid transfection reagent).

Examples of Nucleic Acid Constructs

| Myc-CD4-zeta (1st generation (dimer)) SEQ ID NO: 8 | |
|---|---|
| ATGAACCGGGGAGTCCCTTTTAGGCACTTGCTTCTGGTGCTGCAACTGGC<br>GCTCCTCCCAGCAGCCACTCAGGGAG<u>AGCAGAAGCTGATCTCCGAGGAGG<br>ACC</u>TGAAGAAAGTGGTGCTGGGCAAAAAAGGGGATACAGTGGAACTGACC<br>TGTACAGCTTCCCAGAAGAAGAGCATACAATTCCACTGGAAAAACTCCAA<br>CCAGATAAAGATTCTGGGAAATCAGGGCTCCTTCTTAACTAAAGGTCCAT<br>CCAAGCTGAATGATCGCGCTGACTCAAGAAGAAGCCTTTGGGACCAAGGA<br>AACTTTCCCCTGATCATCAAGAATCTTAAGATAGAAGACTCAGATACTTA<br>CATCTGTGAAGTGGAGGACCAGAAGGAGGAGGTGCAATTGCTAGTGTTCG<br>GATTGACTGCCAACTCTGACACCCACCTGCTTCAGGGGCAGAGCCTGACC<br>CTGACCTTGGAGAGCCCCCTGGTAGTAGCCCCTCAGTGCAATGTAGGAG<br>TCCAAGGGGTAAAAACATACAGGGGGGAAGACCCTCTCCGTGTCTCAGC<br>TGGAGCTCCAGGATAGTGGCACCTGGACATGCACTGTCTTGCAGAACCAG<br>AAGAAGGTGGAGTTCAAAATAGACATCGTGGTGCTAGCTTTCCAGAAGGC<br>CTCCAGCATAGTCTATAAGAAAGAGGGGGAACAGGTGGAGTTCTCCTTCC<br>CACTCGCCTTTACAGTTGAAAAGCTGACGGGCAGTGGCGAGCTGTGGTGG<br>CAGGCGGAGAGGGCTTCCTCCTCCAAGTCTTGGATCACCTTTGACCTGAA<br>GAACAAGGAAGTGTCTGTAAAACGGGTTACCCAGGACCCTAAGCTCCAGA<br>TGGGCAAGAAGCTCCCGCTCCACCTCACCCTGCCCCAGGCCTTGCCTCAG<br>TATGCTGGCTCTGGAAACCTCACCCTGGCCCTTGAAGCGAAAACAGGAAA<br>GTTGCATCAGGAAGTGAACCTGGTGGTGATGAGAGCCACTCAGCTCCAGA<br>AAAATTTGACCTGTGAGGTGTGGGGACCCACCTCCCCTAAGCTGATGCTG<br>AGCTTGAAACTGGAGAACAAGGAGGCAAAGGTCTCGAAGCGGGAGAAGGC<br>GGTGTGGGTGCTGAACCCTGAGGCGGGGATGTGGCAGTGTCTGCTGAGTG<br>ACTCGGGACAGGTCCTGCTGGAATCCAACATCAAGGTTCTGCCCACATGG<br>TCCACCCCGGTG<u>CCTAGGCTGGATCCCAAACTCTGCTACCTGCTGGATGG<br>AATCCTCTTCATCTATGGTGTCATTCTCACTGCCTTGTTCCTGAGAGTGA<br>AGTTCAGCAGGAGCGCAGACGCCCCCGCGTACCAGCAGGGCCAGAACCAG<br>CTCTATAACGAGCTCAATCTAGGACGAAGAGAGGAGTACGATGTTTTGGA<br>CAAGAGACGTGGCCGGGACCCTGAGATGGGGGGAAAGCCGAGAAGGAAGA<br>ACCCTCAGGAAGGCCTGTACAATGAACTGCAGAAAGATAAGATGGCGGAG<br>GCCTACAGTGAGATTGGGATGAAAGGCGAGCGCCGGAGGGGCAAGGGGCA<br>CGATGGCCTTTACCAGGGTCTCAGTACAGCCACCAAGGACACCTACGACG<br>CC</u> | myc (underline)<br>CD4<br><br><br><br><br><br><br><br><br><br><br><br><br><br><br><br><br><br><br><br><br><br><br><br>zeta (Underline) |

| Myc-CD4-CD28-zeta (2nd generation) SEQ ID NO: 9 | |
|---|---|
| ATGAACCGGGGAGTCCCTTTTAGGCACTTGCTTCTGGTGCTGCAACTGGC<br>GCTCCTCCCAGCAGCCACTCAGGGAG<u>AGCAGAAGCTGATCTCCGAGGAGG<br>ACC</u>TGAAGAAAGTGGTGCTGGGCAAAAAAGGGGATACAGTGGAACTGACC<br>TGTACAGCTTCCCAGAAGAAGAGCATACAATTCCACTGGAAAAACTCCAA<br>CCAGATAAAGATTCTGGGAAATCAGGGCTCCTTCTTAACTAAAGGTCCAT<br>CCAAGCTGAATGATCGCGCTGACTCAAGAAGAAGCCTTTGGGACCAAGGA<br>AACTTTCCCCTGATCATCAAGAATCTTAAGATAGAAGACTCAGATACTTA<br>CATCTGTGAAGTGGAGGACCAGAAGGAGGAGGTGCAATTGCTAGTGTTCG<br>GATTGACTGCCAACTCTGACACCCACCTGCTTCAGGGGCAGAGCCTGACC<br>CTGACCTTGGAGAGCCCCCTGGTAGTAGCCCCTCAGTGCAATGTAGGAG<br>TCCAAGGGGTAAAAACATACAGGGGGGAAGACCCTCTCCGTGTCTCAGC<br>TGGAGCTCCAGGATAGTGGCACCTGGACATGCACTGTCTTGCAGAACCAG<br>AAGAAGGTGGAGTTCAAAATAGACATCGTGGTGCTAGCTTTCCAGAAGGC<br>CTCCAGCATAGTCTATAAGAAAGAGGGGGAACAGGTGGAGTTCTCCTTCC<br>CACTCGCCTTTACAGTTGAAAAGCTGACGGGCAGTGGCGAGCTGTGGTGG<br>CAGGCGGAGAGGGCTTCCTCCTCCAAGTCTTGGATCACCTTTGACCTGAA<br>GAACAAGGAAGTGTCTGTAAAACGGGTTACCCAGGACCCTAAGCTCCAGA<br>TGGGCAAGAAGCTCCCGCTCCACCTCACCCTGCCCCAGGCCTTGCCTCAG<br>TATGCTGGCTCTGGAAACCTCACCCTGGCCCTTGAAGCGAAAACAGGAAA<br>GTTGCATCAGGAAGTGAACCTGGTGGTGATGAGAGCCACTCAGCTCCAG<br>AAAAATTTGACCTGTGAGGTGTGGGGACCCACCTCCCCTAAGCTGATGC<br>TGAGCTTGAAACTGGAGAACAAGGAGGCAAAGGTCTCGAAGCGGGAGAAG<br>GCGGTGTGGGTGCTGAACCCTGAGGCGGGGATGTGGCAGTGTCTGCTGAG<br>TGACTCGGGACAGGTCCTGCTGGAATCCAACATCAAGGTTCTGCCCACAT | myc (underline)<br>CD4 |

```
GGTCCACCCCGGTGCCTAGGAAAATTGAAGTTATGTATCCTCCTCCTTAC    CD28 (underline)
CTAGACAATGAGAAGAGCAATGGAACCATTATCCATGTGAAAGGGAAACA
CCTTTGTCCAAGTCCCCTATTTCCCGGACCTTCTAAGCCCTTTTGGGTGC
TGGTGGTGGTTGGTGGAGTCCTGGCTTGCTATAGCTTGCTAGTAACAGTG
GCCTTTATTATTTTCTGGGTGAGGAGTAAGAGGAGCAGGCTCCTGCACAG
TGACTACATGAACATGACTCCCCGCCGCCCCGGGCCCACCCGCAAGCATT
ACCAGCCCTATGCCCCACCACGCGACTTCGCAGCCTATCGCTCCAGAGTG    zeta
AAGTTCAGCAGGAGCGCAGACGCCCCCGCGTACCAGCAGGGCCAGAACCA
GCTCTATAACGAGCTCAATCTAGGACGAAGAGGAGTACGATGTTTTGG
ACAAGAGACGTGGCCGGGACCCTGAGATGGGGGGAAAGCCGAGAAGGAAG
AACCCTCAGGAAGGCCTGTACAATGAACTGCAGAAAGATAAGATGGCGGA
GGCCTACAGTGAGATTGGGATGAAAGGCGAGCGCCGGAGGGGCAAGGGGC
ACGATGGCCTTTACCAGGGTCTCAGTACAGCCACCAAGGACACCTACGAC
GCC
```

The amino acid sequence for the CD28 and CD3 zeta portions of the 2$^{nd}$ generation construct is (SEQ ID NO: 10)
K I E V Met Y P P P Y L D N E K S N G T I I H V K G K H L C P S P L F P G P S K P F W V L V V V G G V L A C Y S L L V T V A F I I F W V R S K R S R L L H S D Y Met N Met T P R R P G P T R K H Y Q P Y A P P R D F A A Y R S R V K F S R S A D A P A Y Q Q G Q N Q L Y N E L N L G R R E E Y D V L D K R R G R D P E Met G G K P R R K N P Q E G L Y N E L Q K D K Met A E A Y S E I G Met K G E R R R G K G

H D G L Y Q G L S T A T K D T Y D A

Host T-Cells

The host T-cells of the invention can be isolated from, e.g., a patient infected with HIV. The host T-cells are transfected or infected with nucleic acid constructs of the invention (e.g., nucleic acid constructs encoding a CIR and, optionally, one or more siRNA constructs). Prior to administration to a patient the T-cells can be expanded in cell culture. In one embodiment, the modified T-cells are administered to the patient from whom they were originally isolated.

In one embodiment, PBMCs are isolated by standard techniques and transduced with a CIR. Cells are administered to the patient in a dose of between 10$^9$ and 10$^{10}$ cells (e.g., 10$^9$, 5×10$^9$, or 10$^{10}$ cells). Cells can be isolated once and expanded for multiple administrations or a separate isolation and transduction can be performed with each round of treatment.

Treatment can be, e.g., a single treatment, monthly treatment, semi-annual treatment, or annual treatment.

Additional Agents

Additional antiviral can be, for example, a protease inhibitor, a reverse transcriptase inhibitor, an integrase inhibitor, a CCR5 antagonist, a fusion inhibitor, or a second maturation inhibitor. The additional antiviral agent can be, without limitation, azidovudine (AZT), didanosine (dideoxyinosine, ddI), d4T, zalcitabine (dideoxycytosine, ddC), nevirapine, lamivudine (epivir, 3TC), saquinavir (Invirase), ritonavir (Norvir), indinavir (Crixivan), and delavirdine (Rescriptor).

Additional Therapies

The methods of the invention can be combined with, e.g., lymphodepletion prior to administration of host T-cells. Furthermore, treatment can also include the administration of one or more cytokines, e.g., IL-2, IL-7, and IL-15.

Experimental Results

Construction of Retroviral Vectors

The chimeric immune T-cell receptor (CIR) of the prior anti-HIV designer T cell trials had the structure of extracellular domain of CD4 (a polypeptide corresponding to amino acids 1-372 of SEQ ID NO:1), transmembrane domain of CD4 (a polypeptide corresponding to amino acids 373-395 of SEQ ID NO:1) and cytoplasmic domain of zeta (a polypeptide corresponding to amino acids 31-142 of SEQ ID NO:3) (Deeks et al. (2002) Mol Ther 5:788-797, Mitsuyasu et al. (2000) Blood 96:785-793) (herein "Hege CIR", FIG. 1). We also designed a signal one-only CIR that is similar to the Hege CIR except that the transmembrane domain of zeta (a polypeptide corresponding to amino acids residues 7-30 of SEQ ID NO:3) was substituted (1$^{st}$ generation CIR, FIG. 1). Lastly, we created a construct that integrates CD28 as well as zeta signaling in a two signal format (2$^{nd}$ generation CIR, FIG. 1). This employs the same extracellular domain of CD4 (a polypeptide corresponding to amino acids 1-372 of SEQ ID NO:1) with a partial extracellular doman/transmembrane domain/cytoplasmic domain of CD28 (a polypeptide corresponding to amino acids 127-234 of SEQ ID NO:2) and is expressed as dimer.

In addition, a c-myc tag (EQKLISEEDL) of human origin is also included in our constructs at the N-terminus of CD4.

1$^{st}$ and 2$^{nd}$ generation CIRs were constructed in the MFG retrovirus vector. Retrovirus was created by ping pong between the E+86 ecotropic and PG13 amphotropic cell lines. PG13 is a helper cell line derived from murine fibroblasts that is used to create vector producer cells (VPC) for retroviral production. VPCs were sorted for the highest transgene expression and viral supernatants were harvested as described Beaudoin et al. ((2008) J Virol Methods 148: 253-259).

Expression of CIRs

Figure 3:
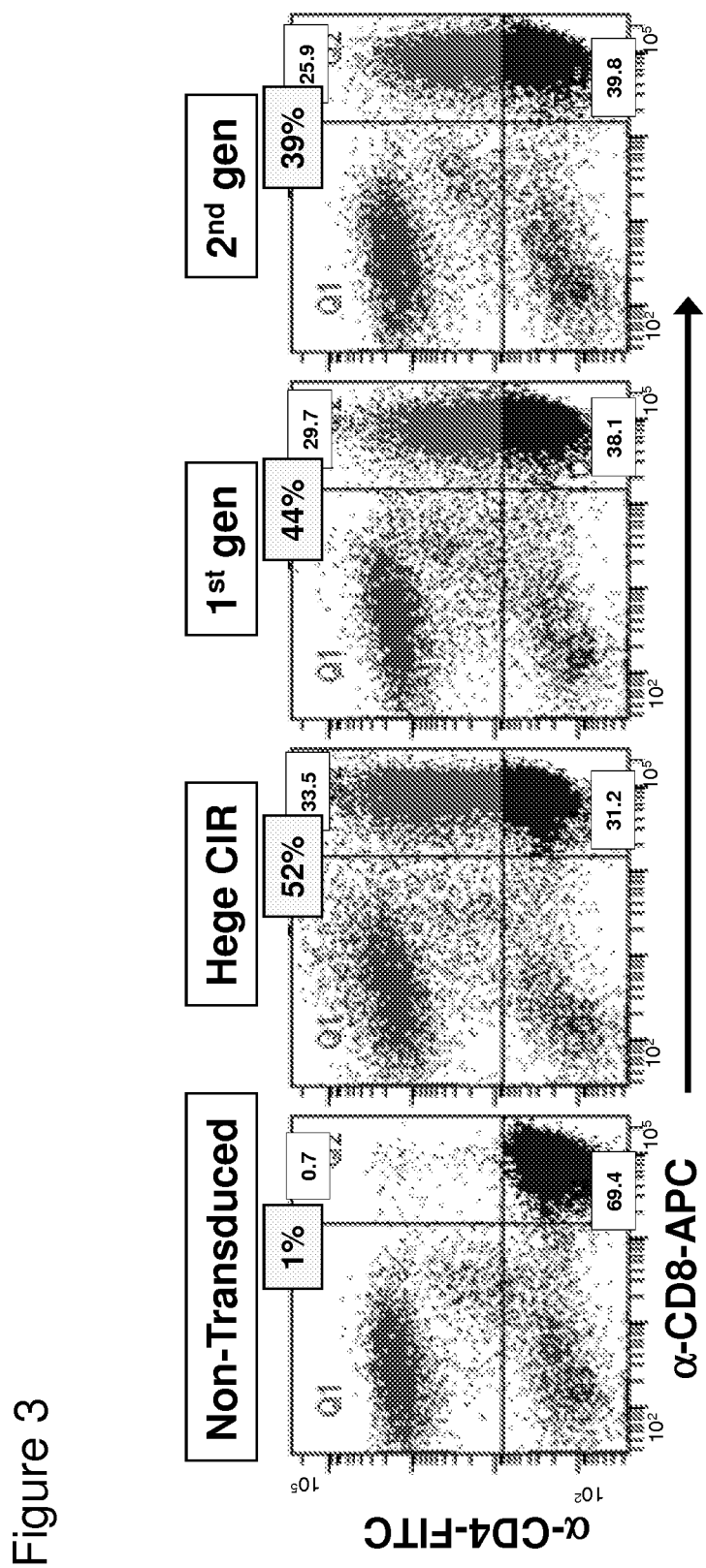
FIG. 3 is a series of graphs showing the cellular surface expression of the indicated CIR. PBMCs were transduced with retrovirus and stained with anti-CD4-FITC and anti-CD8-APC antibodies after four days and analyzed by flow cytometry. % CD8+ cells expressing Hege CIR is 52%, $1^{st}$ generation CIR is 44%, and $2^{nd}$ generation CIR is 39%. A representative experiment of four is shown.

Viral supernatants from PG13 VPCs were used to transduce human PBMCs. PBMCs from normal healthy individuals were purified and activated with anti-CD3 antibody (OKT3) and 100 U/ml IL2 for two days and transduced with retrovirus by spinoculation on a retronectin coated plate. We determined the surface expression of CIRs on CD8+ T-cells by double staining for CD8 and CD4 and determined the transduction rate (as % modified cells, FIG. 3). Transduction of activated human T-cells routinely yield 40 to 70% transduction rates with these anti-HIV CIRs.

Figure 4:
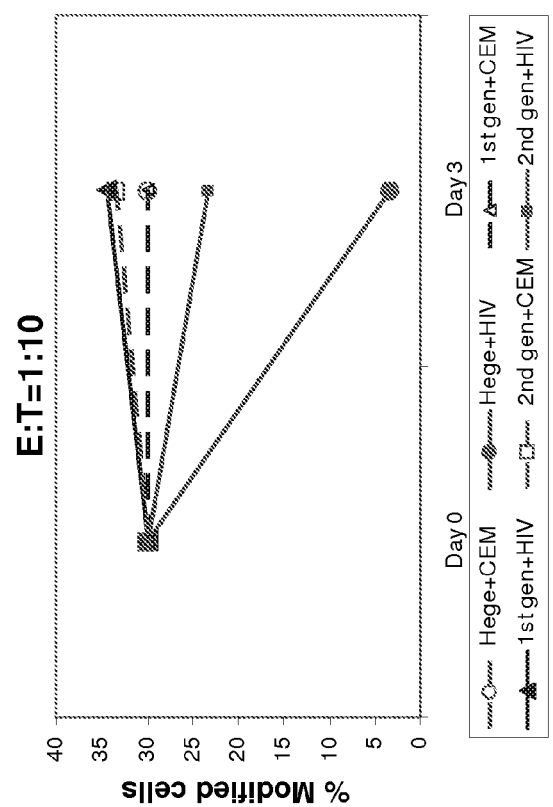
FIG. 4A is a pair of graphs showing survival of the indicated cell type when incubated with HIV-infected CEM-SS cells at the indicated ratio. Transduced PBMCs were co-cultured with HIV-infected CEM-SS cells or uninfected CEM-SS cells at an Effector to Target (E:T) ratio of 1:1 or 1:10. Aliquots of cells were taken from the cultures at day three and stained with anti-CD4 and anti-CD8 antibodies as described above. Data shown is % modified cells (CD8+CIR+) at each time point. A representative of two experiments is shown.
FIG. 4B is a pair of graphs showing flow cytometry analysis from day three for Hege CIR cells. Hege CIR T-cells disappear (Hege+HIV, upper right quadrant) when cultured at an E:T ratio of 1:10. % Modified cells=(Q2/Q2+ Q4) is shown in each plot. (Q2 is upper right quadrant and Q4 is lower right quadrant.)
Figure 4:
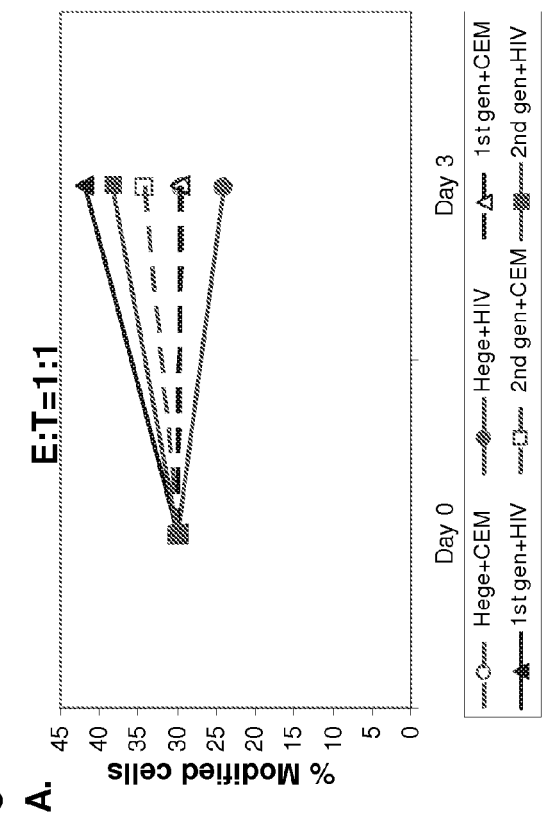
Figure 4:
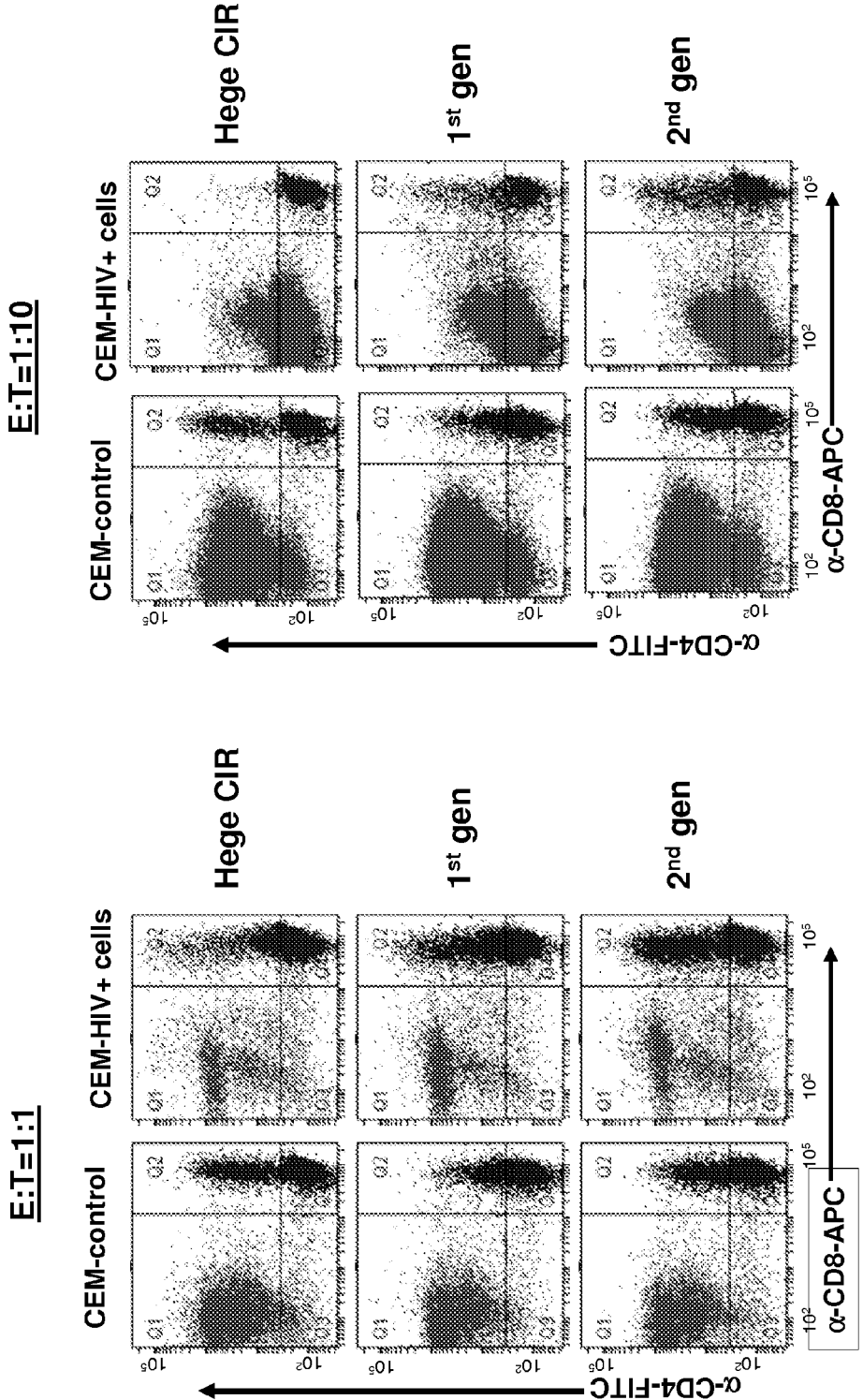
Figure 5:
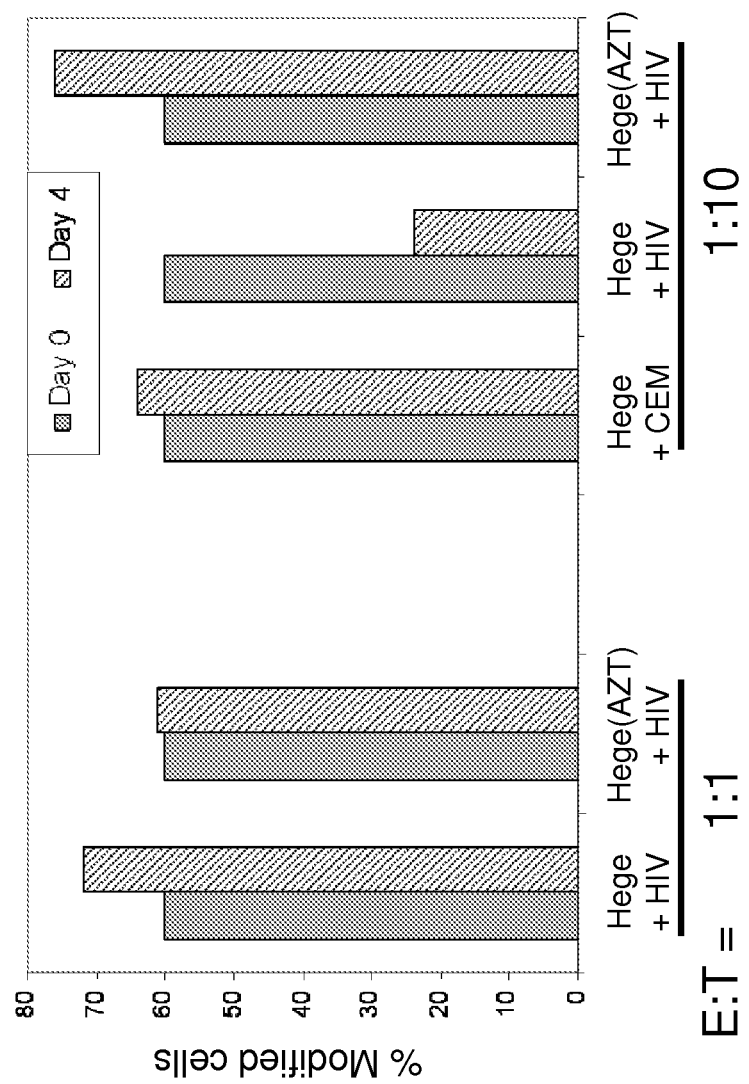
FIG. 5 is a graph showing survival of Hege CIR cells when incubated with HIV-infected CEM-SS cells at the indicated ratio in the presence and absence of AZT. Transduced PBMCs were co-cultured with HIV-infected CEM-SS cells or uninfected CEM-SS cells at an Effector to Target (E:T) ratio of 1:1 or 1:10. Aliquots of cells were taken from the cultures at day three and stained with anti-CD4 and anti-CD8 antibodies as described for FIG. 3. Data shown is % modified cells (CD8+CIR+ cells) from one experiment.

We co-cultured transduced or non-transduced T-cells with CEM-SS HIV+ (chronically infected with HIV-1 IIIB) or HIV-cells (at an E:T ratio of 1:1 or 1:10). We determined the presence of transduced cells in the culture by staining with anti-CD4 and anti-CD8 antibodies. Co-culture of Hege CIR T-cells with CEM-SS HIV+ cells at an E:T ratio of 1:10 induced cell death and all the Hege CIR cells disappeared from the culture by day 3 (FIG. 4). At an E:T ratio of 1:1, Hege CIR T cells were still present in the culture at day 13, with killing of all target cells in the culture (observed by flow cytometry analysis). Cell death observed in the Hege CIR designer T-cells could be either due to heightened sensitivity to Activation Induced Cell Death (AICD) or to HIV infection. To test this, Hege CIR cells were treated with anti-retroviral drug AZT and co-cultured with HIV infected CEM-SS cells. AZT treated Hege CIR cells did not die when co-cultured with higher target ratio (1:10, FIG. 5). These data suggest that Hege CIR cells become infected with HIV and die by either HIV induced apoptosis or killed by other CIR containing T-cells (fratricide). These data suggest and we hypothesize that one of the reasons for the failure of Hege CIR in the clinical trials could be due to highest susceptibility to HIV infection and elimination from the patients.

Susceptibility of Designer T-Cells to HIV Infection

Figure 6:
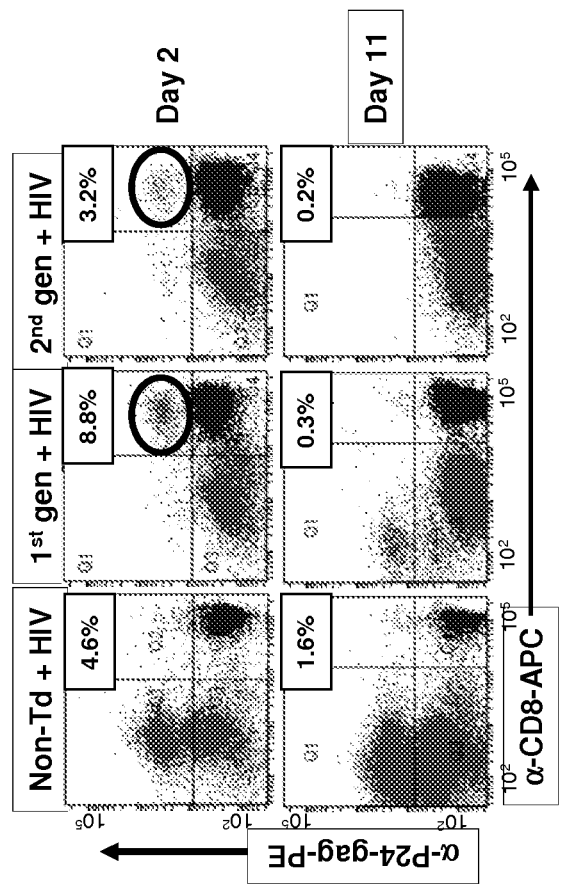
FIG. 6 is a series of graphs showing expression of the indicated markers on the indicated cells when exposed to HIV. Non-transduced or $1^{st}$ and $2^{nd}$ generation CIR transduced T-cells were co-cultured with HIV infected CEM-SS cells for two days and stained with anti-CD8 and anti-p24gag antibodies. An aliquot of unstained cells were washed and continued to culture for another nine days and stained with anti-CD8 and anti-p24gag antibodies. A representative of two experiments is shown. At day two, infected CD8+ cells show as a distinct population (circled) in the $1^{st}$ and $2^{nd}$ generation T-cells compared to non-transduced cells. There is no distinct population of cells seen in non-Td CD8+ cells (day two, upper right quadrant). % modified cells for this experiment is: $1^{st}$ generation=67% and $2^{nd}$ generation=68%.

HIV infects CD4+ T-cells by binding to CD4 receptor and a co-receptor (CXCR4 or CCR5). Since CIR has an extracellular CD4 domain, we postulated that this could be used by HIV to infect all CIR+ T-cells, including CD8+ T-cells. HIV infection of CIR+CD8+ cells was determined by co-culturing CIR containing T-cells with HIV+ CEM-SS cells and staining for p24-gag antigen, an indicator of productive infection. After two days of culture, cells were stained with anti-CD8 and anti-p24 gag antibodies. In contrast to non-transduced cultures, CD8+ cells are infected with HIV in transduced cultures ($1^{st}$ and $2^{nd}$ generation) (FIG. 6). At day 11 we did not detect any HIV infected CD8+ cells in either $1^{st}$ or $2^{nd}$ generation CIR containing T-cells (FIG. 6).

Killing of HIV-Infected Cells by Modified T-Cells.

Figure 7:
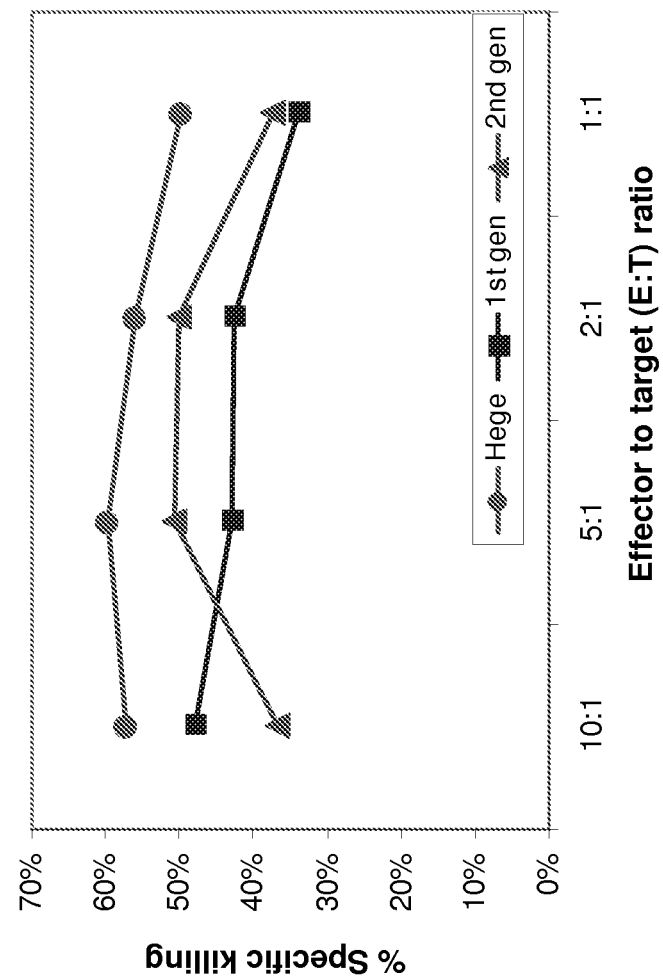
FIG. 7 is a graph showing the percent of specific killing as a function of the ratio of Effector to Target cells. Hege CIR, $1^{st}$, and $2^{nd}$ generation T-cells were cultured with $^{51}Cr$ labeled uninfected or chronically infected with HIV-1 IIIB CEM-SS cells. Cytotoxicity is determined from $^{51}Cr$ release to the culture media after 18 hrs of co-culture at the indicated ratios of Effector to Target, and % specific killing is calculated as follows: (experimental-control)/(maximal-control)× 100. % modified cells for Hege is 47%, for $1^{st}$ generation is 25%, and for $2^{nd}$ generation is 47%. Data shown is representative of two experiments. This is calculated by taking mean value of CEM-SS control as spontaneous release= (Expt-control)/(Max-control).

In order to compare the potencies of Hege CIR, $1^{st}$, and $2^{nd}$ generation anti-HIV CIR in killing of target cells, activated T-cells were transduced as described above. Target cells (HIV-infected or uninfected CEM-SS cells) were labeled with $^{51}$Cr for 5 hrs (50 µCi for $1\times10^6$ cells) and co-cultured with transduced T-cells at indicated E:T ratios for 18 hrs. Hege CIR T-cells and our $1^{st}$ and $2^{nd}$ generation designer T-cells were all equally potent in killing HIV+ target cells (FIG. 7).

Cytokine Secretion by Modified T-Cells.

Figure 8:
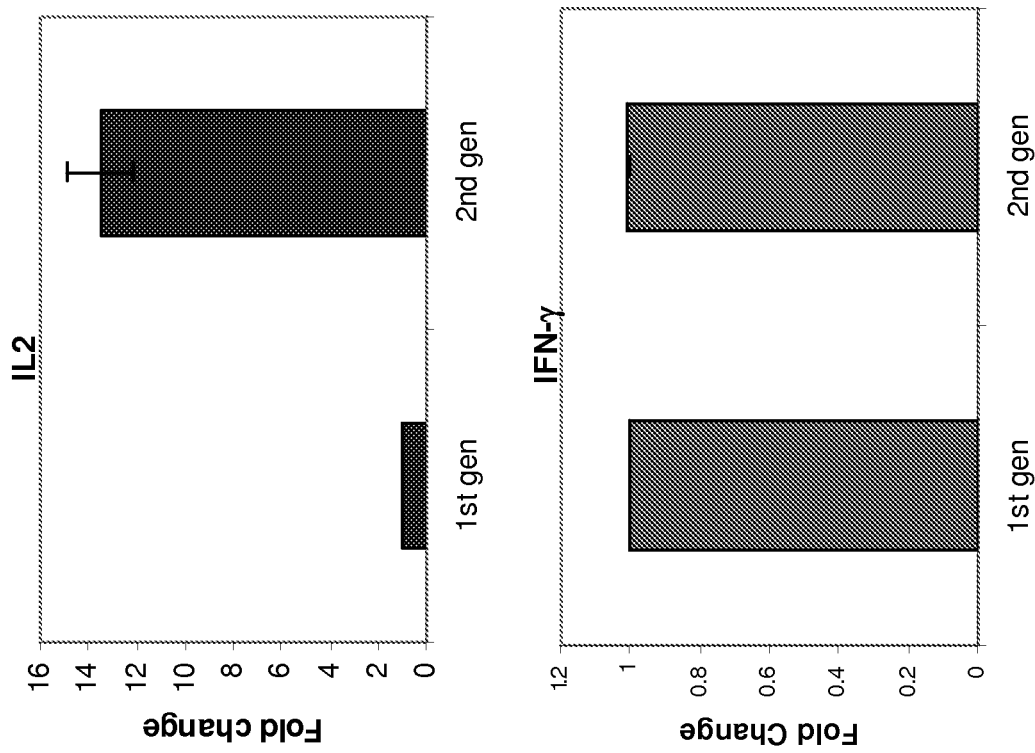
FIG. 8 is a pair of graphs showing the amount of secretion of the indicated cytokine in the indicate cells types. $1^{st}$ and $2^{nd}$ generation T-cells were assayed for IL2 or interferon gamma (IFNγ) secretion by culturing for 24 hrs on anti-CD4 (5 µg/ml) coated plates. Data represented as fold change over $1^{st}$ generation. IL2 data shown is average±SEM of three experiments. IFN-γ data shown is average±SEM of two experiments. % modified cells are similar for $1^{st}$ and $2^{nd}$ generation T-cells.

Human T-cells transduced with $1^{st}$ and $2^{nd}$ generation CIR containing T-cells were tested for their ability to secrete cytokines upon stimulation through the CIR. Transduced or non-transduced T-cells were cultured on anti-CD4 antibody coated plates for 24 hrs. IL2 secretion was measured with an ELISA kit. $2^{nd}$ generation T-cells produced more IL2 than $1^{st}$ generation T-cells when stimulated with anti-CD4 antibody (FIG. 8). In contrast, IFNγ secretion is similar with anti-CD4 stimulation of $1^{st}$ and $2^{nd}$ generation designer T-cells, as is typical for T cell signaling.

Conferring Resistance of Designer T-Cells to HIV Infection

HIV infects CD4+ T-cells by binding to CD4 receptor and a co-receptor (CXCR4 or CCR5). As shown above, CD8+ CIR+ cells ($1^{st}$ and $2^{nd}$ generation) are susceptible to HIV infection (day two, FIG. 6). At day 11 we did not detect any HIV infected CD8+ cells in either $1^{st}$ or $2^{nd}$ generation T-cells (FIG. 6). These data suggest that modified T-cells could kill other HIV infected modified T-cells. Nevertheless, this is a potential source of loss of effector cells to combat HIV and provides a new reservoir to increase patient HIV load. It is therefore becomes important to eliminate or reduce the potential for HIV to infect modified T-cells.

Other Embodiments

Various modifications and variations of the described methods and compositions of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

All publications mentioned in this specification are herein incorporated by reference to the same extent as if each independent publication was specifically and individually incorporated by reference.

What is claimed is:

1. A vector comprising:
   a) a nucleic acid construct encoding a chimeric protein comprising
      (i) an extracellular domain of CD4, or a fragment thereof, wherein the fragment binds specifically to gp120,
      (ii) a transmembrane domain, and
      (iii) a cytoplasmic domain comprising
         a) the cytoplasmic domain of the CD3 zeta chain, or a fragment thereof, wherein the fragment modulates activation of T-cells and
         b) the cytoplasmic domain of CD28,
      wherein the chimeric protein is capable of forming a homodimer when expressed in a T-cell, and
   b) a nucleic acid construct encoding an siRNA specific to an HIV gene, wherein
   the siRNA is capable of suppressing HIV infection and/or replication in a host cell expressing the chimeric protein.

2. The vector of claim 1, wherein the homodimer comprises at least one intermolecular disulfide bond.

3. The vector of claim 1, wherein said transmembrane domain comprises a polypeptide selected from the group consisting of the transmembrane domain of the CD3 zeta chain and the transmembrane domain of CD28.

4. The vector of claim 3, wherein said transmembrane domain comprises amino acids 7-30 of SEQ ID NO:3.

5. The vector of claim 1, wherein said chimeric protein further comprises a c-myc tag.

6. The vector of claim 1, wherein said extracellular domain of CD4 comprises amino acids 1-372 of SEQ ID NO:1.

7. The vector of claim 1, wherein said cytoplasmic domain of the CD3 zeta chain comprises amino acids 31-142 of SEQ ID NO:3.

8. The vector of claim 1, wherein said cytoplasmic domain of CD28 comprises amino acids 180-220 of SEQ ID NO:2.

9. The vector of claim 1, wherein said cytoplasmic domain comprises the amino acid sequence of SEQ ID NO:10.

10. The vector of claim 1, wherein said nucleic acid construct encoding an siRNA comprises a nucleic acid encoding an siRNA against CCR5 or a nucleic acid encoding an siRNA against Tat/Rev.

11. The vector of claim 1, wherein said nucleic acid construct encoding an siRNA comprises a nucleic acid encoding an siRNA against CCR5.

12. The vector of claim 1, wherein said nucleic acid construct encoding an siRNA comprises a nucleic acid encoding an siRNA against Tat/Rev.

13. An isolated host cell comprising the vector of claim 1.

14. The isolated host cell of claim 13, wherein said host cell is a T cell.

15. An isolated host cell comprising the vector of claim 1, wherein said nucleic acid construct encoding an siRNA comprises a nucleic acid encoding an siRNA against CCR5 or a nucleic acid encoding an siRNA against Tat/Rev.

16. The host cell of claim 15, wherein said nucleic acid construct encoding an siRNA comprises a nucleic acid encoding an siRNA against CCR5.

17. The host cell of claim 15, wherein said nucleic acid construct encoding an siRNA comprises a nucleic acid encoding an siRNA against Tat/Rev.

18. A method of treating a patient infected with HIV by administering a composition comprising said host cell of claim 13.

19. The method of claim 18, wherein said host cell is a T cell isolated from said patient.

20. The host cell of claim 15, wherein the host cell is a CD8+ T cell.

* * * * *